United States Patent
Geisser et al.

(10) Patent No.: US 10,570,072 B2
(45) Date of Patent: Feb. 25, 2020

(54) PROCESS FOR THE PREPARATION OF ALCOHOLS FROM ALFA, BETA-UNSATURATED ALDEHYDES AND KETONES

(71) Applicant: GIVAUDAN SA, Vernier (CH)

(72) Inventors: Roger Wilhelm Geisser, Zurich (CH); Nathalie Joset, Duebendorf (CH)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/302,522

(22) PCT Filed: Jun. 12, 2017

(86) PCT No.: PCT/EP2017/064285
§ 371 (c)(1),
(2) Date: Nov. 16, 2018

(87) PCT Pub. No.: WO2017/212069
PCT Pub. Date: Dec. 14, 2017

(65) Prior Publication Data
US 2019/0218164 A1 Jul. 18, 2019

(30) Foreign Application Priority Data
Jun. 10, 2016 (GB) .................................. 1610149.5

(51) Int. Cl.
| | | |
|---|---|---|
| *C07C 29/17* | (2006.01) | |
| *C07C 33/025* | (2006.01) | |
| *B01J 31/24* | (2006.01) | |
| *C07C 31/02* | (2006.01) | |

(52) U.S. Cl.
CPC .......... *C07C 29/175* (2013.01); *B01J 31/2404* (2013.01); *C07C 31/02* (2013.01); *C07C 33/025* (2013.01); *B01J 2231/643* (2013.01); *B01J 2231/645* (2013.01); *B01J 2531/821* (2013.01)

(58) Field of Classification Search
CPC . C07F 15/0046; C07C 29/175; C07C 29/132; C07C 29/14; C07C 29/17; C07C 31/02; C07C 33/025; B01J 2531/821
See application file for complete search history.

(56) References Cited

U.S. PATENT DOCUMENTS 4,320,228 A     3/1982  Horner et al.
7,569,735 B2 *  8/2009  Ino ......................... C07B 41/02
                                                        568/814

FOREIGN PATENT DOCUMENTS

EP          2765126 A1      8/2014

OTHER PUBLICATIONS

Cheng, H., et al., Transfer hydrogenation of citral to citronellol with Ru complexes in the mixed solvent of water and polyethyleneglycol, 2010, Applied Organometallic Chemistry, vol. 24, No. 11, pp. 763-766 (Year: 2010).*
International Search Report and Written Opinion of the International Searching Authority for corresponding application PCT/EP2017/064285 dated Sep. 6, 2017.
GB Search Report for corresponding application GB 1610149.5 dated Apr. 13, 2017.
H. Cheng, et al., "Transfer hydrogenation of citral to citronellol with Ru complexes in the mixed solvent of water and polyethylene glycol", Applied Organometallic Chemistry, 2010, vol. 24, pp. 763-766.
L. G. Melean, et al., "Biphasic Hydrogenation of a,B-unsaturated Aldehydes with Hydrosoluble Rhodium and Ruthenium Complexes", Catalysis Letters, Kluwer Academic Publishers-Plenum Publishers, NE, vol. 141, No. 5, pp. 709-716, 2011.
B. Bachiller-Baeza, et al., "Hydrogenation of Citral on Activated Carbon and High-Surface-Area Graphite-Supported Ruthenium Catalysts Modified with Iron", Journal of Catalysis, vol. 204, pp. 450-459, 2001.
A. Silva, et al., "Hydrogenation of citral over ruthenium-tin catalysts", Applied Catalysis A: Gereral, vol. 241, No. 1-2, pp. 155-165, 2003.
J. Grosselin, et al., "Selective hydrogenation of alpha, beta-unsaturated aldehydes in aqueous organic two-phase solvent systems using ruthenium or rhodium complexes of sulfonated phosphines", Organometallics, vol. 10, No. 7, pp. 2126-2133, 1991.
D. Manikandan, et al."Selective Hydrogenation of Citral Over Noble Metals Intercalated Montmorillonite Catalysts", Catalysys Letters, vol. 123, No. 1-2, pp. 107-114, See especially Table 2, 2008.

* cited by examiner

*Primary Examiner* — Yate' K Cutliff
(74) *Attorney, Agent, or Firm* — Norris McLaughlin, PA

(57) ABSTRACT

A chemoselective process for producing alcohols from α,β-unsaturated aldehydes and ketones is described.

9 Claims, No Drawings

PROCESS FOR THE PREPARATION OF ALCOHOLS FROM ALFA, BETA-UNSATURATED ALDEHYDES AND KETONES

The present invention relates to fragrance ingredients and to methods of forming same. In particular the present invention relates to a method for producing alcohols from α,β-unsaturated aldehydes and ketones.

The reduction of α,β-unsaturated aldehydes is an important reaction, because the possible products, such as saturated aldehydes, and saturated or unsaturated alcohols, have found many uses in fragrances, cosmetics, and pharmaceutical industries; also they constitute relevant intermediates in the synthesis of various fine chemicals. Due to the presence of two or more moieties with similar reactivity the reaction is complicated, in particular, when it is desired that not all moieties react.

Methods of producing alcohols from α,β-unsaturated aldehydes are reported in literature. For example, P. J. Baricelli et al. (*Catalysis Letters* 2011, 141, 709-716) describe a biphasic hydrogenation of α,β-unsaturated aldehydes with a hydrosoluble ionic ruthenium pre-catalyst. Depending on the conditions, mixtures of aldehydes, saturated alcohols and unsaturated alcohols are obtained. Alternatively, alcohols from α,β-unsaturated aldehydes can be produced by transfer hydrogenation in mixed solvents as described, for example, by Zhao et al. (*Applied Organometallic Chemistry* 2010, 24, 763-766). Unfortunately the known processes lack the selectivity with regard to the similar reactivity of the carbonyl group and C=C bonds.

However, for a process to be useful in an industrial context, in particular in fragrance industry, it must achieve the required high chemoselectivity and also proceed with full, or substantially full, conversion of the substrate.

Thus there remains a need for an industrially acceptable process for the preparation of alcohols from α,β-unsaturated aldehydes and ketones further containing one or more di- or trisubstituted olefin carbon-carbon double bond(s), which proceeds with high conversion and with high chemoselectivity for the double bond in α,β-position, without hydrogenation of remaining C=C bond(s).

Surprisingly, applicants found that a two-step process comprising heating α,β-unsaturated aldehydes/ketones containing at least one additional di- and/or trisubstituted carbon-carbon double bond, in the presence of a homogenous catalyst, a base and hydrogen permits a conversion of the α,β-unsaturated aldehydes/ketones selectively into their respective saturated alcohols, without hydrogenation of the remaining double bond(s).

Thus there is provided in a first aspect a process comprising the steps of:
(a) heating to about 30-70° C. (preferably about 40-60° C. (e.g. about 45° C., about 50° C. or about 55° C.) a compound of formula (II)

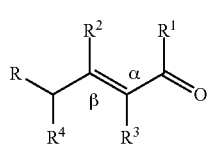

in the presence of hydrogen gas, a base and a homogenous ruthenium catalyst resulting a compound of formula (III)

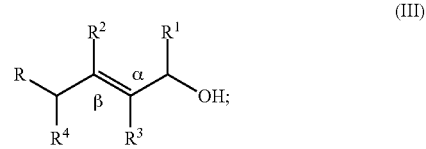

(b) followed by increasing the temperature up to about 100-150° C. (preferably about 110-130° C. (e.g. about 115° C., about 120° C. or about 125° C.), resulting in a compound of formula (I)

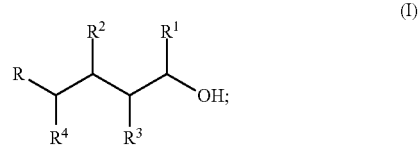

wherein $R^1$ is hydrogen or methyl;
$R^2$ is hydrogen or methyl;
$R^3$ is methyl, or ethyl;
$R^4$ is hydrogen or methyl; and
R is a linear or branched $C_3$-$C_{15}$ alkyl comprising at last one (e.g., 2, or 3 double bonds) non-terminal carbon-to-carbon double bond (such as 3-methyl but-2-enyl, 3,7-dimethyl-octa-2,6-dienyl, 2,3-dimethylbut-2-enyl, but-2-enyl, 2,4,7-trimethylocta-2,6-dienyl, 2-methylpent-2-enyl)

By the term "non-terminal carbon-to-carbon double bond" is meant either a di-substituted vicinal carbon-to-carbon double bond, a tri-substituted carbon-to-carbon double bond, or a tetra-substituted carbon-to-carbon double bond.

Non-limiting examples are compounds of formula (II) wherein $R^1$ is hydrogen.

Further, non-limiting examples are compounds of formula (II) wherein $R^1$, and $R^2$ are hydrogen.

Further, non-limiting examples are compounds of formula (II) wherein $R^1$ is hydrogen and $R^2$ is methyl.

Further, non-limiting examples are compounds of formula (II) wherein $R^1$ is hydrogen and $R^2=R^3$.

Further, non-limiting examples are compounds of formula (II) wherein the α,β-unsaturated double bond is preferably in E-configuration.

Further, non-limiting examples are compounds of formula (II) wherein $R^3$ and $R^4$ are methyl, and the α,β-unsaturated double bond is preferably in E-configuration.

Further, non-limiting examples are compounds of formula (II) wherein R is a branched $C_5$-$C_{15}$ alkyl (including $C_6$, $C_7$, $C_8$, $C_9$, $C_{10}$ and $C_{11}$ alkyl) comprising at least one (e.g., 2, or 3 double bonds) tri-substituted carbon-to-carbon double bond.

Further, non-limiting examples of compounds of formula (II) are compounds selected from 3,7-dimethylocta-2,6-dienal (R is $C_5$-alkyl comprising one tri-substituted double bond); 2,4,7,11-tetramethyldodeca-2,6,10-trienal (R is $C_{10}$-alkyl comprising two tri-substituted double bonds); 2,3,6,7-tetramethylocta-2,6-dienal (R is $C_6$-alkyl comprising one tetra-substituted double bond); 2,4-dimethylocta-2,6-dienal (R is $C_4$-alkyl comprising one vicinal di-substituted double bond); 3,7,11-trimethyldodeca-2,6,10-trienal (R is $C_{10}$-alkyl comprising two tri-substituted double bonds); 3,6,8,11-tetramethyldodeca-2,6,10-trienal (R is $C_{11}$-alkyl comprising two tri-substituted double bonds); and 2,4,6-trimethylnona-2,6-dienal (R is $C_6$-alkyl comprising one tri-substituted double bond).

The ruthenium catalyst employed in the present invention may be any of those disclosed in EP1970360, which document, for the purpose of disclosing the ruthenium catalysts contained therein, is hereby incorporated by reference.

In a particular embodiment of the present invention, the process proceeds in the presence of a homogeneous ruthenium (II) catalyst. The term "homogeneous catalyst" is well known to the person skilled in the art, and refers to catalysts which are present in the same phase as the substrate.

In one embodiment the homogeneous ruthenium (II) catalyst is a complex (A)

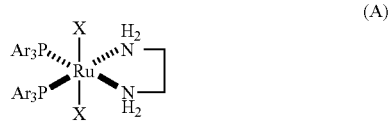

(A)

with two triarylphosphines, a diamine and two electronegative ligands (e.g. X may be a halogen such as Cl, Br, and I).

In one specific embodiment the ruthenium (II) catalyst is a compound of formula (A) wherein Ar is para-methyl phenyl.

In another specific embodiment the ruthenium (II) catalyst is $RuCl_2(PPh_3)_2$(ethylene-diamine), which is commercially available or may be prepared in-situ from commercially available reagents by a process as described, for example, by Takeshi Ohkuma et al. (*J. Am. Chem. Soc.* 1995, 117, 10417).

To be of high commercial value, the molar ratio between substrate (compound of formula (II)) and the catalyst is at least 500:1, preferably between about 1 000:1 and about 10 000:1, or even higher.

To obtain high yields, step (b) follows after substantially all substrate (II) has been converted to compounds of formula (III), for example, 88% or more (including 90, 92, 95, 98, 99%) of the substrate has been converted, as measured by gas chromatography (GC) relative peak area. For example, by 50% conversion is meant that the peak area of the starting material (compound of formula (II)) is reduced by 50% under the same GC conditions. The conversion can be measured by techniques known in the art. For example, it can be measured by taking a sample of the reaction mixture after a given time and analyzing said mixture by GC analysis. Optionally, one may also monitor the reaction by nuclear magnetic resonance (NMR) spectroscopy or thin layer chromatography (TLC).

In addition to the high chemoselectivity of the processes described herein, a further advantage of the process is that it can be performed almost without solvent. The only solvent necessary is to assist in the solubility of the base. Suitable solvents include alkyl alcohols, such as methanol, ethanol, iso-propanol, n-butanol.

Suitable bases include alkali metal compounds selected from the group consisting of hydroxides (such as sodium hydroxide, lithium hydroxide, potassium hydroxide, cesium hydroxide and the like), alcoholates (such as sodium methoxide, potassium ethoxide, and the like), carboxylates (such as sodium acetate, potassium acetate and the like), carbonates and hydrogencarbonates including sodium carbonate, sodium hydrogen carbonate, lithium carbonate, potassium carbonate, cesium carbonate and the like.

In one embodiment the process of the invention is carried out in the presence of a base selected from sodium hydroxide, sodium methoxide and potassium hydroxide.

The invention is now further described with reference to the following non-limiting examples. These examples are for the purpose of illustration only and it is understood that variations and modifications can be made by one skilled in the art.

EXAMPLE 1

Under air atmosphere NaOMe (30 wt % in MeOH) (19.8 g, 4.0 wt %, 0.11 mol) was added to a 1 L stainless steel autoclave containing $RuCl_2(PPh_3)_2$(ethylenediamine) catalyst (0.197 g, 0.26 mmol), 2,4,7-trimethylocta-2,6-dienal (94.2% purity, E/Z, 50:1) (499.2 g, 3.00 mol) and i-PrOH (10 g). While stirring with an overhead stirrer the autoclave was flushed three times with $N_2$, then three times with $H_2$, then put under $H_2$ pressure (41.0 bar) and heated to 50° C. After 3.9 hours almost full C=O conversion was observed (>95.5%) by GC (relative peak area) resulting in 2,4,7-trimethylocta-2,6-dienol (compound of formula (III)). The temperature of the autoclave was raised to 120° C. (temperature reached within 0.2 h). After a further 3.9 h the reaction was stopped, cooled to room temperature, the pressure released and the autoclave was flushed three times with $N_2$. The yellow homogeneous mixture was washed with water (210 mL). The aqueous phase was extracted with methyl tertbutyl ether (350 mL). The organic layer was washed with brine (100 mL), water (100 mL) and dried over $MgSO_4$ (50.0 g), filtered and concentrated in vacuo. To the obtained yellow liquid paraffin oil (12.3 g) was added and after distillation using a Vigreux column, a colorless liquid of 2,4,7-trimethyloct-6-en-1-ol was obtained (426.2 g, 92.4% purity, 81.9 mol % chemical yield, boiling point=75° C. at 0.5 mbar). In addition to the main product, traces of the intermediate 2,4,7-trimethylocta-2,6-dienol, and double bond isomers thereof have been identified at low concentrations, such as (E)/(Z)-2,4,7-trimethyloct-3,6-dien-1-ol, and (E)/(Z)-2,4,7-trimethylocta-4,6-dienal.

EXAMPLE 2

A 10 mL glass vial was charged with 1 g of 2,4,6-trimethylnona-2,6-dienal (99% purity, E/Z, 32:1), 1 mL cyclohexane, 2.1 mg of $Cl_2Ru(PPh_3)_2$(ethylenediamine) and 210 μL of NaOMe (30 wt % in MeOH). The vial was equipped with a stirring bar and sealed. The vial was flushed with $N_2$ (1 bar) and then three times with $H_2$ (1 bar) before setting the pressure of $H_2$ (40 bar). The reaction mixture was heated at 50° C. for 2 h and then 120° C. for a further 2 h. Once cooled, the $H_2$ overpressure was purged and the vial flushed with $N_2$. The reaction mixture was quenched with $H_2O$, the layers separated and the aqueous phase extracted twice with MTBE. The combined organic phases were washed with brine, dried over $MgSO_4$, filtered and solvent removal provided crude alcohol which was purified by distillation using Kugelrohr (T=100° C., t=15 min, p=0.2 mbar) to provide a colorless liquid of 2,4,6-trimethylnon-6-en-1-ol (450 mg, 82% purity, 36.9 mol % chemical yield).

COMPARISON EXAMPLE 1

Under air atmosphere NaOMe (30 wt % in MeOH) (19.8 g, 4.0 wt %, 0.11 mol) is added to a 1 L stainless steel autoclave containing RuCl$_2$(PPh$_3$)$_2$(ethylenediamine) catalyst (0.197 g, 0.26 mmol), 2,4,7-trimethylocta-2,6,dienal (94.2% purity, E/Z, 50:1) (499.35 g, 2.78 mol) and i-PrOH (10 g). While stirring with an overhead stirrer the autoclave is flushed three times with N$_2$, then three times with H$_2$, then put under H$_2$ pressure (41.0 bar) and heated to 120° C. After 22 hours almost full C═O conversion is observed (>95.5%) measured by GC (relative peak area). The reaction is stopped, cooled to room temperature, the pressure released and the autoclave is flushed three times with N$_2$. The yellow homogeneous mixture is washed with water (210 mL). The aqueous phase is extracted with methyl tertbutyl ether (350 mL). The organic layer is washed with brine (100 mL), water (100 mL) and dried over MgSO$_4$ (50.0 g), filtered and concentrated in vacuo. To the obtained yellow liquid is added paraffin oil (12.3 g) and after distillation using a Vigreux column, a colorless liquid of 2,4,7-trimethyloct-6-en-1-ol is obtained (298.5 g, 89.1% purity, 69 mol % chemical yield).

The invention claimed is:

1. A process comprising the steps of:
   (a) heating to about 30-70° C. a compound of formula (II)

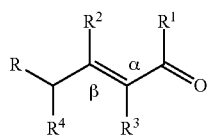

(II)

in the presence of hydrogen gas, a base and a homogeneous ruthenium catalyst and thereby forming a compound of formula (III)

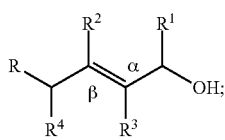

(III)

(b) followed by increasing the temperature up to about 100-150° C., and thereby forming a compound of formula (I)

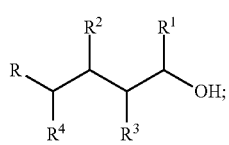

(I)

wherein in each of formula (I), (II) and (III):
R$^1$ is hydrogen or methyl;
R$^2$ is hydrogen or methyl;
R$^3$ is methyl, or ethyl;
R$^4$ is hydrogen or methyl; and
R is a linear or branched C$_3$-C$_{10}$ alkyl comprising at least one non-terminal carbon-to-carbon double bond.

2. The process according to claim 1 wherein the base is an alkali metal compound.

3. The process according to claim 1 wherein the temperature is increased after at least 88% of the compound of formula (II) has been converted to the respective alcohol of formula (III).

4. The process according to claim 1, wherein the catalyst is a homogeneous ruthenium (II) catalyst.

5. The process according to claim 4 wherein the homogeneous ruthenium (II) catalyst is a Ru complex comprising two triarylphosphines, a diamine and two electronegative ligands.

6. The process according to claim 1, wherein the ruthenium catalyst is RuCl$_2$(PPh$_3$)$_2$(ethylene-diamine) or RuCl$_2$(P(para-methyl phenyl)$_3$)$_2$(ethylene-diamine).

7. A process according to claim 1 wherein the α,β-unsaturated double bond of the compound of formula (II) is in E-configuration.

8. A process according to claim 1 wherein:
R$^1$ is hydrogen;
R$^2$ is hydrogen;
R$^3$ is methyl;
R$^4$ is methyl; and
R is selected from the group consisting of 3-methyl but-2-enyl, 3,7-dimethylocta-2,6-dieneyl, 2,3-dimethylbut-2-enyl, but-2-enyl, 2,4,7-trimethylocta-2,6-dieneyl, and 2-methylpent-2-enyl.

9. A process according to claim 8 wherein R is 3-methyl but-2-enyl.

* * * * *